United States Patent [19]
Nomura et al.

[11] Patent Number: 5,980,571
[45] Date of Patent: Nov. 9, 1999

[54] SUBSTITUTE-HEART CONTROL APPARATUS

[75] Inventors: Takashi Nomura, Komaki, Japan; Douglas W. Blakely, San Antonio, Tex.; Setsuo Takatani, Yamagata; Keizo Kawaguchi, Komaki, both of Japan

[73] Assignee: Colin Corporation, Aichi-ken, Japan

[21] Appl. No.: 08/989,267

[22] Filed: Dec. 11, 1997

[51] Int. Cl.$^6$ ..................................................... A61M 1/12
[52] U.S. Cl. ................................................. 623/3; 600/17
[58] Field of Search ................................. 623/3; 600/16, 600/17; 415/900; 601/153

[56] References Cited

U.S. PATENT DOCUMENTS

| | | |
|---|---|---|
| 3,878,567 | 4/1975 | Purdy . |
| 4,231,354 | 11/1980 | Kurtz et al. . |
| 5,224,478 | 7/1993 | Sakai et al. . |
| 5,319,738 | 6/1994 | Shima et al. . |

FOREIGN PATENT DOCUMENTS

| | | | |
|---|---|---|---|
| 23 55 966 | 5/1975 | Germany . | |
| A-1-214340 | 8/1989 | Japan . | |
| 3-210272 | 9/1991 | Japan | 600/17 |
| 91/08006 | 6/1991 | WIPO | 600/17 |

OTHER PUBLICATIONS

Geier M. et al., "Control System for an Artificial Heart with Mean–Value Model of the Cardiovascular System", vol. 39, No. 12, Dec. 1994, pp. 316–320.

*Primary Examiner*—David H. Willse
*Attorney, Agent, or Firm*—Oliff & Berridge, PLC

[57] ABSTRACT

A substitute-heart control apparatus for controlling a substitute heart provided in a living body, including an information obtaining device which non-invasively obtains, from the living body, physical information relating to blood circulation in the living body, and a control device which supplies, to the substitute heart, a control signal to control a cardiac output that is a volume of blood outputted from the substitute heart per unit time, based on the physical information obtained by the information obtaining device, according to a predetermined relationship between cardiac output and physical information.

11 Claims, 2 Drawing Sheets

SUBSTITUTE-HEART CONTROL APPARATUS

BACKGROUND OF THE INVENTION

1. Field of the Invention

The present invention relates to a control apparatus which controls a substitute heart which is provided in a living body, such as a human being, in place of the natural heart of the living body.

2. Related Art Statement

When a human being has a problem with the function of his or her natural heart, a substitute heart such as an artificial heart or a natural heart of a different living body may be provided temporarily or permanently in the human being, in place of his or her natural heart, for substituting the function of the natural heart. However, it has been a conventional manner that the substitute heart provided in the human being is controlled by a control device or a pacemaker such that the substitute heart only performs a prescribed blood outputting operation.

Generally, the blood circulation in the circulatory organ of a human being changes among his or her different physical or mental states and/or under external physical or mental stimuli experienced in his or her daily life. However, if a substitute heart provided in a patient is so controlled as to perform only a prescribed blood outputting operation, the circulatory organ of the patient cannot appropriately respond to the different physical or mental states, respectively, or the different external stimuli, respectively. Thus, the patient may be inhibited from doing some sorts of exercises such as running or swimming, or experiencing some sorts of external stimuli in his or her daily life. That is, the patient may not enjoy quality of life as a human being.

SUMMARY OF THE INVENTION

It is therefore an object of the present invention to provide a substitute-heart control apparatus which contributes to reducing restrictions on the daily life of a living body who has, in place of his or her natural heart, a substitute heart controlled thereby and thus improving his or her quality of life.

According to a first feature of the present invention, there is provided a substitute-heart control apparatus for controlling a substitute heart provided in a living body, comprising an information obtaining device which non-invasively obtains, from the living body, physical information relating to blood circulation in the living body; and a control device which supplies, to the substitute heart, a control signal to control a cardiac output that is a volume of blood outputted from the substitute heart per unit time, based on the physical information obtained by the information obtaining device, according to a predetermined relationship between cardiac output and physical information.

In the substitute-heart control apparatus in accordance with the first feature, the control device supplies, to the substitute heart, the control signal to control the cardiac output of the substitute heart, based on the physical information obtained by the information obtaining device, according to the predetermined relationship between cardiac output and physical information. Therefore, the circulatory organ of the living body who has the substitute heart controlled by the present control apparatus can appropriately respond to his or her various mental or physical states and/or to various external stimuli which he or she experiences in his or her daily life, in contrast to a conventional substitute heart which only performs a prescribed blood outputting operation. Thus, the present control apparatus can reduce restrictions on the daily life of the living body, thereby contributing to improving his or her quality of life.

According to a second feature of the present invention, the predetermined relationship between cardiac output and physical information comprises a relationship which is predetermined based on a cardiac output of the natural heart of the living body, and the physical information obtained before the natural heart of the living body is substituted by the substitute heart. Since the relationship between cardiac output and physical information is predetermined based on values of cardiac output of the natural heart of the living body, and values of the physical information obtained before the natural heart of the living body is substituted by the substitute heart, the relationship is specific to the living body and well reflects his or her personal physical or mental characteristics.

According to a third feature of the present invention, the predetermined relationship between cardiac output and physical information comprises a relationship between fluctuations of heart rate and physical information which is obtained by learning fluctuations of heart rate of the natural heart of the living body, and the physical information obtained before the natural heart of the living body is substituted by the substitute heart, and the control device comprises a heart-rate control device which supplies, to the substitute heart, the control signal to cause fluctuations of heart rate of the substitute heart, based on the physical information obtained by the information obtaining device, according to the relationship between fluctuations of heart rate and physical information. In this case, the heart-rate control device can cause fluctuations of heart rate of the substitute heart of the living body which correspond to a current state of his or her autonomic nerve system. Thus, the living body can feel a very comfortable operation of the substitute heart, in contrast to a convectional substitute heart which just performs a prescribed operation.

According to a fourth feature of the present invention, the heart-rate control device comprises a neural network which learns a plurality of constants of a function based on the fluctuations of heart rate of the natural heart of the living body, and the physical information obtained before the natural heart of the living body is substituted by the substitute heart, the function defining the relationship between fluctuations of heart rate and physical information, the neural network generating, as an output signal therefrom, the control signal to cause the fluctuations of heart rate of the substitute heart, based on the physical information obtained by the information obtaining device, as an input signal thereto, according to the function having the learned constants. In this case, the neural network can easily learn the relationship between fluctuations of heart rate and physical information, based on the fluctuations of heart rate of the natural heart of the living body, and the physical information obtained before the natural heart of the living body is substituted by the substitute heart.

According to a fifth feature of the present invention, the information obtaining device comprises at least one of a device which measures a body temperature of the living body, a device which measures a blood pressure of a peripheral portion of the living body, a device which measures a time interval between successive two heartbeat-synchronous pulses obtained from a peripheral portion of the living body, a device which obtains a waveform indicative of blood pressure of a peripheral portion of the living body, a device which measures a velocity at which a pulse wave propagates through an artery of the living body, a device which measures a blood oxygen saturation of the living body, a device which measures an amount of perspiration of the living body per unit time, a device which measures a respiratory frequency of the living body, a device which measures an amount of physical motion of the living body per unit time, and a device which obtains a statistic value of at least one of the body temperature, the blood pressure, the pulse interval, the blood-pressure waveform, the pulse-wave velocity, the blood oxygen saturation, the perspiration amount, the respiratory frequency, and the physical-motion amount. Each of those physical-information obtaining devices can non-invasively and easily obtain physical information relating to the blood circulation in the circulatory organ of the living body such as a human being.

According to a sixth feature of the present invention, the substitute heart comprises an artificial heart, and the control device comprises means for supplying, to the artificial heart, the control signal to control a heart rate of the artificial heart based on the physical information obtained by the information obtaining device, according to a predetermined relationship between heart rate and physical information as the predetermined relationship between cardiac output and physical information.

According to a seventh feature of the present invention, the substitute heart comprises an artificial heart, and the control device comprises means for supplying, to the artificial heart, the control signal to control a volume of blood outputted from the artificial heart per beat, based on the physical information obtained by the information obtaining device, according to a predetermined relationship between beat volume and physical information as the predetermined relationship between cardiac output and physical information.

According to an eighth feature of the present invention, the substitute heart comprises a natural heart transplanted from a different living body, and wherein the control device comprises means for supplying, to the transplanted natural heart, the control signal to control a heart rate of the transplanted natural heart based on the physical information obtained by the information obtaining device, according to a predetermined relationship between heart rate and physical information as the predetermined relationship between cardiac output and physical information. In this case, the control signal may electrically stimulate the cardiac muscle of the transplanted natural heart, either directly or indirectly via, e.g., a pacemaker, so that the heart constricts and then relaxes to output the blood through the aorta.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Figure 1:
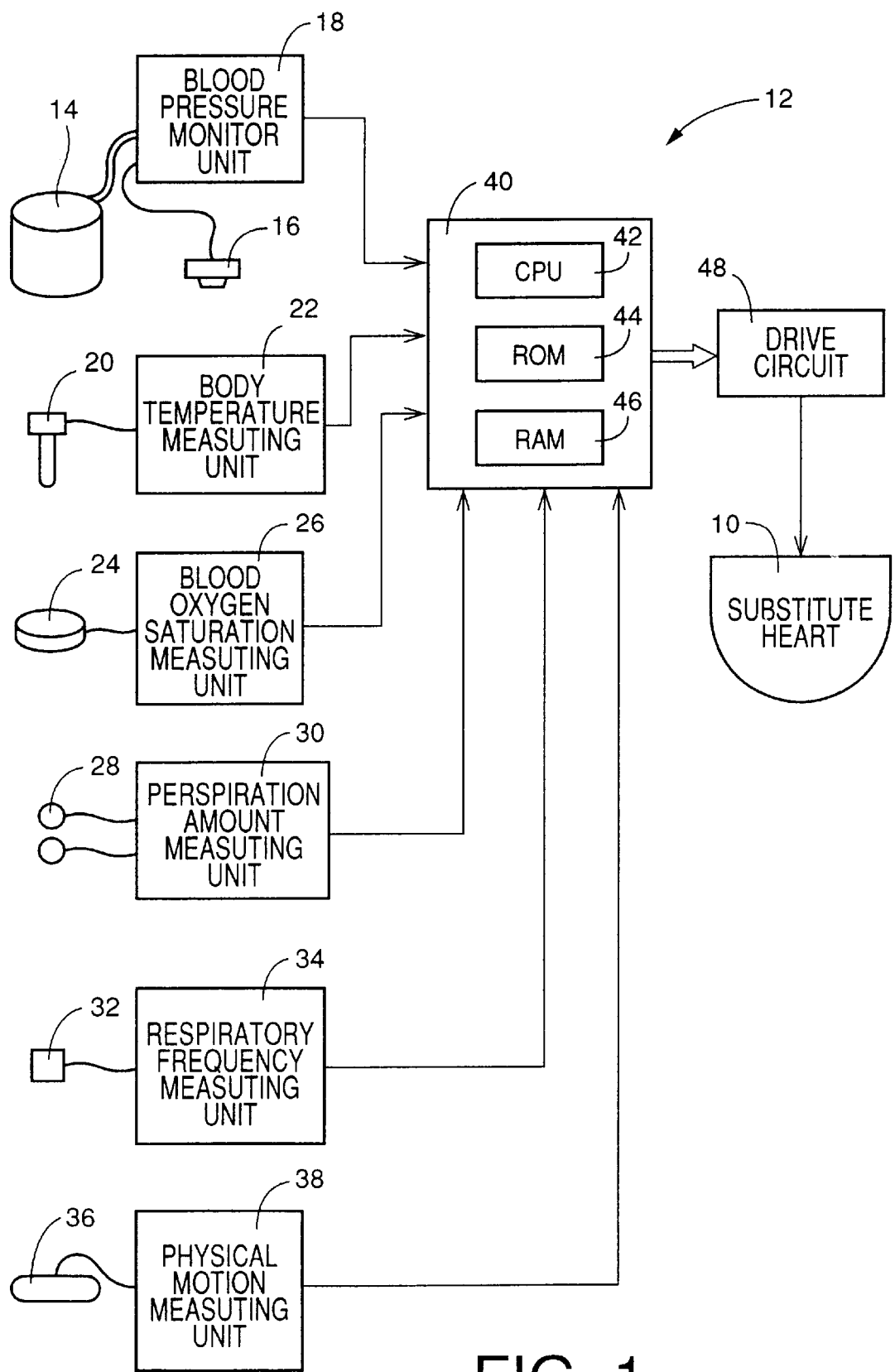
FIG. 1 is an illustrative view of a substitute-heart control apparatus to which the present invention is applied.
Figure 2:
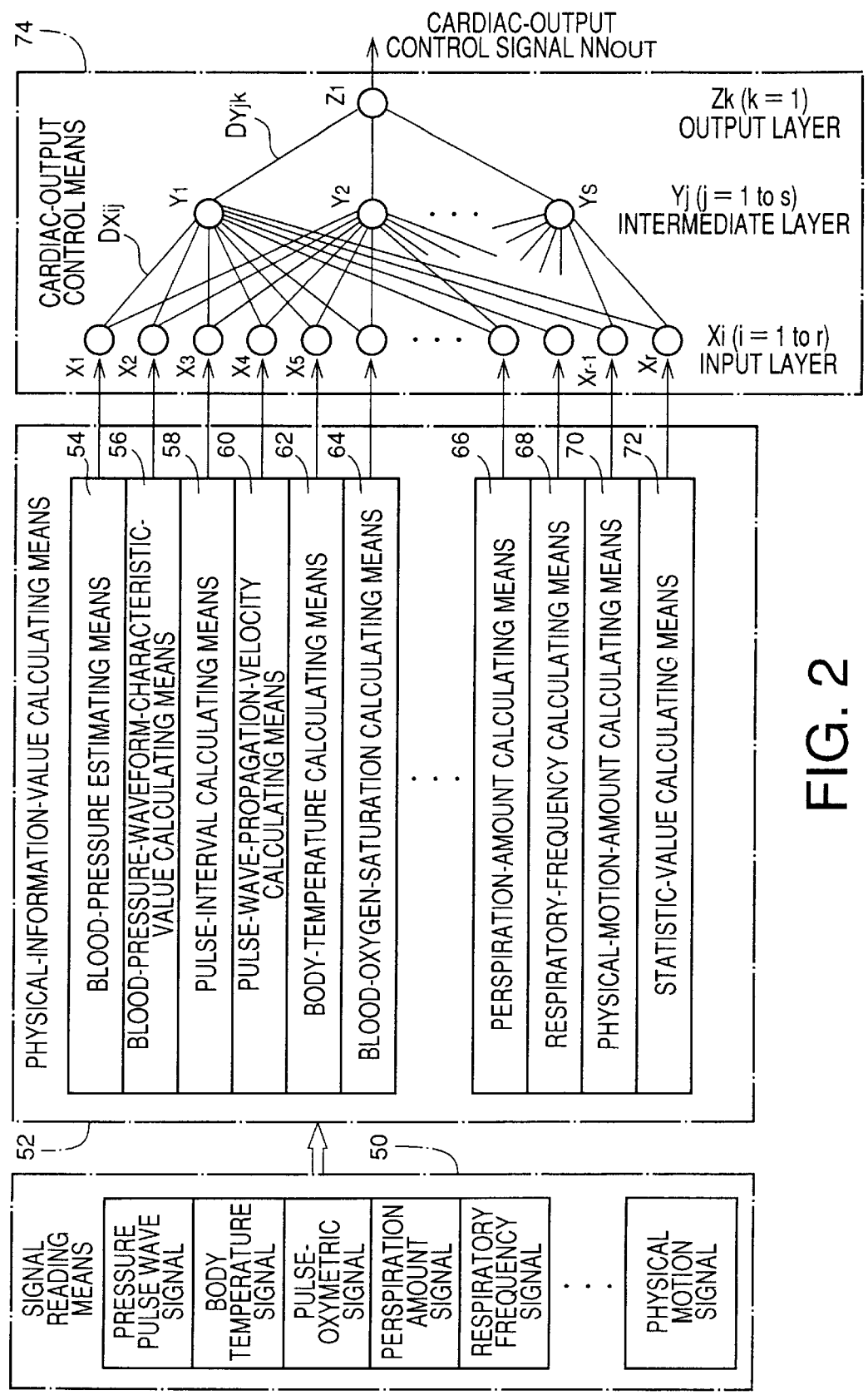
FIG. 2 is a block diagram illustrating various control functions of a control circuit of the control apparatus of FIG. 1.

Referring to FIGS. 1 and 2, there will be described a substitute-heart control apparatus 12 to which the present invention is applied. The control apparatus 12 controls an amount of blood outputted from a substitute heart 10 per unit time, that is, cardiac output, CO (1/min), of the same 10. The substitute heart 10 is placed in a living body such as a human being in place of his or her natural heart. The substitute heart 10 may be a total-substitution-type artificial heart, an assist-type artificial heart, or the natural heart of a different living body. The total-substitution-type artificial heart is a man-made pump which totally substitutes the function of the natural heart of the living body; the assist-type artificial heart may include a U-shaped pump, a cylinder-type pump, a sac-type pump, a diaphragm-type pump, or a cup-type pump, and assists the function or functions of the right and/or left hearts of the living body; and the natural heart of different living body may be a natural heart transplanted from the different living body such as a human being or an anthropoid ape.

The control apparatus 12 may be placed either outside or inside the living body. The control apparatus 12 includes (A) a blood pressure ("BP") monitor unit 18 which includes an inflatable cuff 14 adapted to be wound around an upper arm of the living body, and a pressure-pulse-wave ("PPW") detector probe 16 adapted to be worn on the forehand of the same or different arm of the living body such that the PPW probe 16 is pressed against the radial artery of the forehand via the skin tissue; (B) a body-temperature ("BT") measuring unit 22 including a BT measuring probe 20 adapted to be worn on the living body; (C) a blood-oxygen-saturation ("BOS") measuring unit 26 including a BOS measuring probe 24 which emits lights toward the living body and detects the lights scattered by the same; (D) a perspiration-amount ("PA") measuring unit 30 including electrodes 28 adapted to be put on the skin of the living body; (E) a respiratory-frequency ("RF") measuring unit 34 including an RF sensor 32 which detects the changes of wind speed at the nares of the living body; and (F) a physical-motion ("PM") measuring unit 38 including a PM sensor 36 which measures the amount of position change of the living body, i.e., the amount of physical motion of the living body. In addition, the control apparatus 12 includes a control circuit 40 which supplies the substitute heart 10 with a cardiac-output control signal, $NN_{OUT}$, as a drive signal to drive the same 10, based on the BP values, EBP(t), successively provided by the BP monitor unit 18, the BT values, $T_B$, provided by the BT measuring unit 22, the BOS values, $SpO_2$, provided by the BOS measuring unit 26, the PA values, $S_W$, provided by the PA measuring unit 30, the RF values, BR, provided by the RF measuring unit 34, and the PM values, $M_B$, provided by the PM measuring unit 38.

The inflatable cuff 14 includes a belt-like cloth bag and a rubber bag accommodated in the cloth bag, and is worn on the living body such as a patient such that the cuff 14 is wound around an upper arm of the patient. The PPW probe 16 is detachably attached to the wrist of the same or different arm of the patient with the help of bands (not shown), detects a pressure pulse wave ("PPW") indicative of a pressure in the radial artery running in the wrist, and outputs a PPW signal representative of the detected PPW. The BP monitor unit 18 includes an air pump (not shown) and a deflation control valve (not shown) which are operated according to commands supplied from the control circuit 40. When standard BP values are measured for calibrating the PPW probe 16, the air pump is operated for supplying pressurized air to the cuff 14 and thereby quickly increasing the air pressure in the cuff 14, and then the deflation control valve is operated to discharge the pressurized air from the cuff 14 in such a manner that the air pressure of the cuff 14 is decreased at a low rate of about 3 mmHg/sec. During this low-rate deflation of the cuff 14, a systolic, a mean, and a diastolic BP value of the living subject are measured as the standard BP values, according to the well-known oscillometric method. When this BP measurement ends, the deflation control valve is so operated as to deflate quickly the cuff 14. The BP monitor unit 18 additionally includes an air-pressure control circuit (not shown) which establishes and maintains, according to commands supplied from the control circuit 40, an optimum air pressure in a pressure chamber (not shown) for pressing the PPW sensor 16 against the radial artery. The BP monitor unit 18 supplies the control circuit 40 with the PPW signal which is outputted from the PPW sensor 16 and which indicates the blood pressure in the radial artery of the patient.

The BT measuring unit 22 includes a BT measuring circuit (not shown) which cooperates with a thermistor (not shown) of the BT measuring probe 20 to provide a BT measuring bridge, and supplies the control circuit 40 with a BT signal indicative of the detected BT value, $T_B$, of the patient.

The BOS measuring probe 24 emits, toward the skin tissue of the patient (i.e., the blood present in the skin tissue), a first light having the wavelength, $\lambda_1$, of about 730 nm and a second light having the wavelength, $\lambda_2$, of about 880 nm. The absorption coefficient of the 730 nm-wavelength light is not influenced by the blood oxygen saturation of the patient, whereas that of the 880 nm-wavelength light is influenced by the blood oxygen saturation. The BOS measuring probe 24 detects the first and second lights scattered by the skin tissue, determines the alternating and direct components of each of the detected scattered first and second lights, and supplies the control circuit 40 with a pulse-oxymetric signal including a signal indicative of the ratio, $AC_R/DC_R$, of the alternating component, $AC_R$, to the direct component, $DC_R$, of the first (red) light, and a signal indicative of the ratio, $AC_{IR}/DC_{IR}$, of the alternating component, $AC_{IR}$, to the direct component, $DC_{IR}$, of the second (infrared) light.

The PA measuring unit 30 measures an electric resistance between the two electrodes 28 put on the skin of the patient, determines the perspiration amount of the patient per unit time based on the measured electric resistance according to a predetermined relationship between amount of perspiration and electric resistance, and supplies the control circuit 40 with a PA signal indicative of the determined PA value.

The RF measuring unit 34 outputs, to the control circuit 40, an RF signal which is received from the RF sensor 32 adapted to be worn at the nares of the patient and which indicates the changes of wind speed at the nares of the patient.

The PM measuring unit 38 outputs, to the control circuit 40, a PM signal which is received from the PM sensor 36 adapted to be worn on the patient and which indicates the amount of physical motion of the patient.

The control circuit 40 is provided by a so-called microcomputer including a central processing unit (CPU) 42, a read only memory (ROM) 44, a random access memory (RAM) 46, and an input-and-output (I/O) port (not shown). The CPU 42 processes the received signals according to the control programs pre-stored in the ROM 44, while utilizing the temporary-storage function of the RAM 46. More specifically described, the CPU 46 determines, based on the signals supplied from the various physical-information obtaining devices 18, 22, 26, 30, 34, 38, a heart rate, HR (/min), for the substitute heart 10, that is, the number of beats per unit time for the heart 10, and outputs a cardiac-output control signal $NN_{OUT}$ indicative of the determined heart rate HR, to a drive circuit 48, which outputs, to the heart 10, a drive signal at a period corresponding to the control signal $NN_{OUT}$.

FIG. 2 is a block diagram representing various functions of the control circuit 40 of the substitute-heart control apparatus 12 constructed as described above. First, the control circuit 40 functions as a signal reading means 50 which reads the PPW signal, the BT signal, the pulse-oxymetric signal, the PA signal, the RF signal, and the PM signal which are supplied from the respective physical-information obtaining devices 18, 22, 26, 30, 34, 38.

Second, the control circuit 40 functions as a physical-information-value calculating means 52 which includes a BP estimating means 54, a BP-waveform-characteristic-value calculating means 56, a pulse-interval calculating means 58, a pulse-wave-propagation-velocity calculating means 60, a BT calculating means 62, a BOS calculating means 64, a PA calculating means 66, an RF calculating means 68, a PM calculating means 70, and a statistic-value calculating means 72. The BP estimating means 54 successively estimates a systolic, a mean, and a diastolic BP value EBP(t) of the patient based on each of successive heartbeat-synchronous pulses of the PPW signal read by the signal reading means 50. The BP-waveform-characteristic-value calculating means 56 calculates, based on the waveform of PPW signal, a value, SI, indicative of a characteristic of the PPW-signal waveform indicative of the blood pressure in the radial artery of the patient. The pulse-interval calculating means 58 calculates, based on the PPW signal, a time interval, $T_{MM}$, between respective maximum (or minimum) magnitudes of successive two heartbeat-synchronous pulses of the PPW. The pulse-wave-propagation-velocity calculating means 60 calculates a pulse-wave velocity, PWV, at which a pulse wave propagates through an artery of the patient, based on, e.g., the PPW signal and pulse-oxymetric signal read by the reading means 50. The BT calculating means 62 calculates a BT value $T_B$ of the patient based on the BT signal read by the reading means 50. The BOS calculating means 64 calculates a BOS value $SpO_2$ of the patient based on the pulse-oxymetric signal read by the reading means 50. The PA calculating means 66 calculates a perspiration amount $S_W$ of the patient per unit time, based on the PA signal read by the reading means 50. The RF calculating means 68 calculates a RF value BR of the patient, based on the RF signal read by the reading means 50. The PM calculating means 70 calculates an amount $M_B$ of physical motion of the patient per unit time, based on the PM signal read by the reading means 50. The statistic-value calculating means 72 calculates a statistic value from each sort of physical-information values EBP(t), SI, $T_{MM}$, PWV, $T_B$, $SpO_2$, $S_W$, BR, $M_B$.

The BP estimating means 54 operates like the blood pressure monitor device disclosed in Japanese Patent Application laid open for inspection under Publication No. 1(1989)-214340. In short, the BP estimating means 54 measures standard BP values (e.g., systolic BP value, $BP_{SYS}$, mean BP value, $BP_{MEAN}$, and diastolic BP value, $BP_{DIA}$) of the patient, based on variation of respective amplitudes of heartbeat-synchronous pulses of the pulse wave which is detected through the cuff 14 while the pressure of the cuff 14 applied to the upper arm of the patient is changed at a low rate of about 3 mmHg/sec, according to the well-known oscillometric method. Alternatively, the BP estimating means 54 may be one which measures standard BP values according to the well-known Korotkoff-sound method in which Korotkoff sounds are detected using a microphone from the cuff 14 for determining systolic and diastolic BP values of the patient. In addition, the BP estimating means 54 determines, in advance, a relationship between BP values and PPW magnitudes, $P_M$, based on the measured standard BP values and magnitudes (e.g., a maximum, a mean, and a minimum magnitude) $P_M$ of one heartbeat-synchronous pulse of the PPW detected by the PPW probe 16, and successively estimates BP values (e.g., estimated systolic BP value, $MBP_{SYS}$, estimated mean BP value, $MBP_{MEAN}$, and estimated diastolic BP value, $MBP_{DIA}$) of the patient based on magnitudes $P_M$ of each of heartbeat-synchronous pulses of the PPW which is detected by the PPW sensor 16 after the determination of the BP-$P_M$ relationship. Thus, the BP estimating means 54 provides a pressure signal indicative of the successively determined BP values EBP(t).

The waveform of each heartbeat-synchronous pulse of the PPW signal provided by the PPW sensor 16 or the pressure signal provided by the BP estimating means 54 has a so-called "notch" which occurs after the waveform takes its maximum magnitude and which has the mean magnitude of the waveform. The BP-waveform-characteristic-value calculating means 56 may determine, as the waveform characteristic value SI, the maximum magnitude of the waveform, the rate of decrease of magnitude of a portion following the occurrence of the maximum magnitude or the notch, or the ratio of an upper portion of the amplitude of the waveform above the notch to a lower portion of the same below the notch. The waveform characteristic value SI changes as the resistance of the peripheral artery (e.g., radial artery) of the patient changes.

The pulse-interval calculating means 58 calculates, as the pulse interval $T_{MM}$, a time interval between respective maximum or minimum magnitudes of successive two heartbeat-synchronous pulses of the PPW signal provided by the PPW sensor 16 or the pressure signal provided by the BP estimating means 54. The pulse interval $T_{MM}$ changes in relation with the hardness of the peripheral artery (e.g., radial artery) of the patient.

The pulse-wave-propagation-velocity calculating means 60 calculates a time interval, DT, between the detection of a heartbeat-synchronous pulse of the PPW by the PPW sensor 16 and the detection of a corresponding heartbeat-synchronous pulse of the pulse-oxymetric signal by the BOS measuring probe 24 which is worn on a peripheral portion (e.g., finger) of the patient downstream of the PPW sensor 16, and calculates the pulse-wave-propagation velocity PWV by dividing the distance between the two locations where the PPW sensor 16 and the BOS sensor 24 are placed on the patient, respectively, with the calculated time interval DT.

The BT calculating means 62 determines a BT value $T_B$ based on the BT signal supplied from the BT measuring unit 22, according to a predetermined relationship between BT and magnitude (i.g., voltage) of BT signal.

The BOS calculating means 64 operates like the reflection-type blood-oxygen-saturation measuring device disclosed in U.S. Pat. No. 5,224,478. In short, the BOS calculating means 64 calculates, based on the pulse-oxymetric signal supplied from the BOS measuring unit 26, the ratio, $R=(AC_R/DC_R)/(AC_{IR}/DC_{IR})$, of the ratio $AC_R/DC_R$ of the alternating component $AC_R$ to the direct component $DC_R$ of the first (red) light to the ratio $AC_{IR}/DC_{IR}$ of the alternating component $AC_{IR}$ to the direct component $DC_{IR}$ of the second (infrared) light, and calculates a BOS value $SpO_2$ based on the calculated ratio R, according to a predetermined relationship between BOS and ratio R.

The PA calculating means 66 calculates the perspiration amount PA of the patient per unit time, based on the PA signal provided by the PA measuring unit 30.

The RF calculating means 68 calculates the RF value BR (/min) of the patient, i.e., the number of respirations of the patient per minute, based on the period of change of the RF signal which is provided by the RF sensor 32 worn at the nares of the patient and which indicates the changes of wind speed at the nares of the patient.

The PM-amount calculating means 70 calculates the PM amount $M_B$ (W/min) of the patient, i.e., the amount of physical motion of the patient per minute, based on the PM signal supplied from the PM sensor 36 worn on the patient.

The statistic-value calculating means 72 calculates a statistic value, A, based on each sort of physical-information values EBP(t), SI, $T_{MM}$, PWV, $T_B$, $SpO_2$, $S_W$, BR, $M_B$ which are calculated by the physical-information calculating means 52 (54–70) during each of successive time intervals of about several seconds to several tens of seconds. For example, the statistic-value calculating means 72 calculates, as the statistic values, the maximum value, the average value, the standard deviation, and/or the difference between the maximum and minimum values, of the values of each sort EBP(t), SI, $T_{MM}$, PWV, $T_B$, $SpO_2$, $S_W$, BR, $M_B$ which are obtained during each time interval. FIG. 2 shows that the statistic-value calculating means 72 has a single output which is connected to a single neuron unit, $X_i$, of an input layer, $X_i$ (i=1 to r), of a neural network, NN, of a cardiac-output ("CO") control means 74 as a function of the control circuit 40. However, in the case where the statistic-value calculating means 72 calculates a plurality of sorts of statistic values, the means 72 should be equipped with a corresponding number of signal outputs which should be connected to a corresponding number of neuron units X of the input layer $X_i$, respectively.

Each time the above-indicated sorts of physical-information values EBP(t), SI, $T_{MM}$, PWV, $T_B$, $SpO_2$, $S_W$, BR, $M_B$ are calculated by the physical-information calculating means 52 (54–72), the neural network NN of the CO control means 74 produces and outputs a cardiac-output control signal $NN_{OUT}$ to control the operation of the substitute heart 10 (e.g., electric pump incorporated in an artificial heart, or pacemaker connected to a transplanted natural heart), based on those values EBP(t), SI, $T_{MM}$, PWV, $T_B$, $SpO_2$, $S_W$, BR, $M_B$.

The neural network NN of the CO control means 74 may be provided by a software, i.e., a computer program, or a hardware, i.e., an electronic-component circuit each of which models a group of neurons of a living organism such as a human being. For example, the CO control means 74 may be equipped with a neural network NN having a three-layer hierarchical structure as shown in FIG. 2. More specifically described, the neural network NN includes an input layer consisting of neuron units $X_i$ (i=a natural number of 1 to r), an intermediate layer consisting of neuron units $Y_j$ (j=a natural number of 1 to s), and an output layer consisting of a single neuron unit $Z_k$ (k=1). The neurons $X_i$ of the input layer are connected to the respective outputs of the individual physical-information calculating means 54, 56, 58, 60, 62, 62, 64, 66, 68, 70, 72, respectively. Each of the first-layer neuron units $X_i$ is connected to the intermediate-layer neuron units $Y_j$ via respective connector elements $D_{Xij}$ which have respective connection coefficients (i.e., weights), $W_{Xij}$, and each of the intermediate-layer neuron units $Y_j$ is connected to the output-layer neuron units $Z_k$ via respective connector elements $D_{Yjk}$ which have respective connection coefficients (i.e., weights), $W_{Yjk}$.

The neural network NN is a pattern-association-type system which has learned the connection coefficients (weights) $W_{Xij}$ and the connection coefficients (weights) $W_{Yjk}$, according to a so-called "reverse error propagation learning" algorithm, before the substitute heart 10 is placed in the patient, in place of his or her natural heart. More specifically described, the physical-information obtaining devices 18, 22, 26, 30, 34, 38 are used to obtain the various sorts of physical information from the patient with his or her natural heart, and a heart-rate (HR) measuring device (not shown) is used to measure a HR value of the patient, when the patient is in each of various physical or mental conditions (e.g., running, walking, or surprised condition) which he or she may take in his or her daily life. The neural-network machine NN learns those conditions of the patient by using, as the input signals thereto, the various sorts of physical information obtained from the patient in each patient's condition, using the HR values measured from the patient in the same condition, as reference signals to be compared with the output signals therefrom, and adjusting the weights $W_{Xij}$, $W_{Yjk}$ so that the neuron network NN provides the output signal indicative of the same CO value as that of the natural heart of the patient in the same condition. Therefore, when the substitute heart 10 is placed in the patient in place of his or her natural heart and the present substitute-heart control apparatus 12 is operated for controlling the cardiac output CO of the heart 10, the neuron network NN of the control circuit 10 has fixed values as the weights $W_{Xij}$, $W_{Yjk}$, that is, a fixed relationship between cardiac output CO and physical information. In the present embodiment, the cardiac output CO is defined by the heart rate HR. The HR values obtained from the patient under each condition contains periodic changes (i.e., so-called "fluctuations") characteristic of that condition. Therefore, the above relationship contains a relationship between the fluctuations of the heart rate HR of the patient under each of his or her conditions and the various sorts of physical information. In the case where the stroke volume, $SV_D$, that is the volume of blood outputted per stroke (i.e., heartbeat) from the substitute heart 10, is different from that, $SV_N$, of the natural heart of the patient, the HR values, HR X K, obtained by modifying the actually measured HR values are used for establishing the weights $W_{Xij}$, $W_{Yjk}$ of the neuron network NN. The constant K which is equal to the ratio, $SV_N/SV_D$, is used to modify the actual HR values, for equalizing the cardiac output CO of the substitute heart 10 to that of the natural heart of the patient.

As is apparent from the foregoing description, in the present embodiment, the CO control means 74 supplies the substitute heart 10 of the patient with the control signal $NN_{OUT}$ to control the cardiac output CO of the heart 10, based on the physical information calculated by the physical-information calculating means 52, according to the predetermined relationship between cardiac output CO and physical information. The substitute heart 10 of the patient is not operated at a prescribed heart rate HR as in the known manner. That is, the circulatory organ of the patient with the substitute heart 10 under the control of the control apparatus 12 operates in various ways corresponding to his or her various physical or mental states and/or various stimuli from his or her daily life. Therefore, in his or her daily life, the patient can do various exercises and can enjoy various stimuli, and accordingly can improve his or her quality of life as a human being.

In the present embodiment, the relationship (i.e., weights or constants $W_{Xij}$, $W_{Yjk}$) employed in the CO control means 74 is obtained by learning the various sorts of physical information and the HR values (or the CO values) which are obtained from the patient before the natural heart of the patient is replaced by the substitute heart 10. Therefore, this relationship is specific to the individual patient and is very useful in controlling the cardiac output CO of the substitute heart 10 placed in the patient.

In addition, in the present embodiment, the relationship (i.e., constants $W_{Xij}$, $W_{Yjk}$) employed in the CO control means 74 is obtained by learning the various sorts of physical information and the fluctuations of the HR values which are obtained from the patient before the natural heart of the patient is replaced by the substitute heart 10. Therefore, the CO control means 74 can cause, according to the relationship, fluctuations to the heart rate HR of the substitute heart 10. The fluctuations of heart rate HR of the natural heart of the patient are caused by the autonomic nerve of the patient. Thus, the substitute heart 10 in the patient operates like his or her natural heart, and accordingly the patient enjoys very comfortable life.

Moreover, in the present embodiment, the CO control means 74 is equipped with the neural network NN having the relationship defined by the constants $W_{Xij}$, $W_{Yjk}$ which are obtained by learning the various sorts of physical information and the fluctuations of the HR values which are obtained from the patient before the natural heart of the patient is replaced by the substitute heart 10. That is, this relationship is a function which provides the output signal $NN_{OUT}$ of the neural network NN based on the input signals supplied from the physical-information calculating means 52. Therefore, the neural network NN can easily learn the relationship based on the various sorts of physical information and the CO values which are obtained from the patient before the natural heart of the patient is replaced by the substitute heart 10.

Furthermore, in the present embodiment, the physical-information calculating means 52 can provide one or more of the body temperature $T_B$ of the patient, the blood pressure EBP(t) of the peripheral portion of the patient, the pulse interval $T_{MM}$ obtained from the peripheral portion of the patient, the characteristic value SI of the waveform indicative of the blood pressure of the peripheral portion of the patient, the arterial-pulse-wave propagation velocity PWV, the blood oxygen saturation $SpO_2$, the perspiration amount $S_W$ of the patient, the respiratory frequency BR of the patient, the physical motion amount $M_B$ of the patient, and the statistic value or values A of the body temperature $T_B$, the blood pressure EBP(t), the pulse interval $T_{MM}$, the waveform characteristic value SI, the pulse-wave velocity PWV, the blood oxygen saturation $SpO_2$, the perspiration $S_W$, the respiratory frequency BR, and the physical-motion amount $M_B$. Those sorts of physical information each of which changes in relation with the blood circulation in the patient can be easily and non-invasively obtained from the patient. Therefore, the above-indicated relationship can be easily determined based on those sorts of physical information.

While the present invention has been described in its preferred embodiment, the invention may be otherwise embodied.

For example, the physical-information obtaining devices 18, 22, 26, 30, 34, 38 may additionally include a sensor which measures the concentration of catecholamine, angiotensin, and/or lactic acid present in the blood of the patient. Those substances influence the blood pressure of the patient. In the latter case, therefore, the substitute heart 10 can be controlled with higher accuracy and reliability.

In the illustrated embodiment, the CO control means 74 is equipped with the neural network NN which is completed by learning the relationship between cardiac output CO and physical information based on the data obtained before the natural heart is removed from the patient. However, the neural network NN may be replaced by a table which defines a relationship between cardiac output CO and physical information and which is prepared based on the data obtained before the natural heart is removed from the patient. The table may be stored in the ROM of the control circuit 40. In this case, the substitute heart 10 is controlled by the control circuit 40 based on the actual physical information according to the table stored in the ROM.

In the illustrated embodiment, the CO control means 74 controls the cardiac output CO of the substitute heart 10, by controlling the period of constriction and relaxation of the heart 10. However, in the case where the substitute heart 10 is equipped with a variable-output-volume pump, the CO control means 74 may control the output volume of the heart 10 in each action thereof. In the latter case, too, the CO control means 74 can control the output volume of the substitute heart 10 per unit time.

It is to be understood that the present invention may be embodied with other changes, improvements, and modifications that may occur to those skilled in the art without departing from the scope and spirit of the invention defined in the appended claims.

What is claimed is:

1. A substitute-heart control apparatus for controlling a substitute heart provided in a living body, comprising:

an information obtaining device which non-invasively obtains, from the living body, physical information relating to blood circulation in the living body; and a control device which supplies, to the substitute heart, a control signal to control a cardiac output that is a volume of blood outputted from the substitute heart per unit time, based on the physical information obtained by the information obtaining device, according to a predetermined relationship between cardiac output and physical information, wherein the predetermined relationship between cardiac output and physical information comprises a relationship which is predetermined based on a cardiac output of the natural heart of the living body, and the physical information non-invasively obtained by the information obtaining device before the natural heart of the living body is substituted by the substitute heart.

2. A substitute-heart control apparatus according to claim 1, wherein the relationship predetermined before the natural heart of the living body is substituted by the substitute heart comprises a relationship between fluctuations of heart rate and physical information which is obtained by learning fluctuations of heart rate of the natural heart of the living body, and the physical information obtained before the natural heart of the living body is substituted by the substitute heart, and wherein the control device comprises a heart-rate control device which supplies, to the substitute heart, the control signal to cause fluctuations of heart rate of the substitute heart, based on the physical information obtained by the information obtaining device, according to the relationship between fluctuations of heart rate and physical information.

3. A substitute-heart control apparatus according to claim 2, wherein the heart-rate control device comprises a neural network which learns a plurality of constants of a function based on the fluctuations of heart rate of the natural heart of the living body, and the physical information obtained before the natural heart of the living body is substituted by the substitute heart, the function defining the relationship between fluctuations of heart rate and physical information, the neural network generating, as an output signal therefrom, the control signal to cause the fluctuations of heart rate of the substitute heart, based on the physical information obtained by the information obtaining device, as an input signal thereto, according to the function having the learned constants.

4. A substitute-heart control apparatus according to claim 1, wherein the information obtaining device comprises at least one of a device which measures a body temperature of the living body, a device which measures a blood pressure of a peripheral portion of the living body, a device which measures a time interval between successive two heartbeat-synchronous pulses obtained from a peripheral portion of the living body, a device which obtains a waveform indicative of blood pressure of a peripheral portion of the living body, a device which measures a velocity at which a pulse wave propagates through an artery of the living body, a device which measures a blood oxygen saturation of the living body, a device which measures an amount of perspiration of the living body per unit time, a device which measures a respiratory frequency of the living body, a device which measures an amount of physical motion of the living body per unit time, and a device which obtains a statistic value of at least one of the body temperature, the blood pressure, the pulse interval, the blood-pressure waveform, the pulse-wave velocity, the blood oxygen saturation, the perspiration amount, the respiratory frequency, and the physical-motion amount.

5. A substitute-heart control apparatus according to claim 1, wherein the substitute heart comprises an artificial heart, and wherein the control device comprises means for supplying, to the artificial heart, the control signal to control a heart rate of the artificial heart based on the physical information obtained by the information obtaining device, according to a predetermined relationship between heart rate and physical information as the predetermined relationship between cardiac output and physical information.

6. A substitute-heart control apparatus according to claim 1, wherein the substitute heart comprises an artificial heart, and wherein the control device comprises means for supplying, to the artificial heart, the control signal to control a volume of blood outputted from the artificial heart per beat, based on the physical information obtained by the information obtaining device, according to a predetermined relationship between beat volume and physical information as the predetermined relationship between cardiac output and physical information.

7. A substitute-heart control apparatus according to claim 1, wherein the substitute heart comprises a natural heart transplanted from a different living body, and wherein the control device comprises means for supplying, to the transplanted natural heart, the control signal to control a heart rate of the transplanted natural heart based on the physical information obtained by the information obtaining device, according to a predetermined relationship between heart rate and physical information as the predetermined relationship between cardiac output and physical information.

8. A substitute-heart control apparatus for controlling a substitute heart provided in a living body, comprising:

an information obtaining device which non-invasively obtains, from the living body, physical information relating to blood circulation in the living body; and a control device which supplies, to the substitute heart, a control signal to control a cardiac output that is a volume of blood outputted from the substitute heart per unit time, based on the physical information obtained by the information obtaining device, according to a predetermined relationship between cardiac output and physical information, wherein the predetermined relationship between cardiac output and physical information comprises a relationship between fluctuations of heart rate and physical information which is obtained by learning fluctuations of heart rate of the natural heart of the living body, and the physical information obtained before the natural heart of the living body is substituted by the substitute heart, wherein the control device comprises a heart-rate control device which supplies, to the substitute heart, the control signal to cause fluctuations of heart rate of the substitute heart, based on the physical information obtained by the information obtaining device, according to the relationship between fluctuations of heart rate and physical information, wherein the heart-rate control device comprises a neural network which learns a plurality of constants of a function based on the fluctuations of heart rate of the natural heart of the living body, and the physical information obtained before the natural heart of the living body is substituted by the substitute heart, the function defining the relationship between fluctuations of heart rate and physical information, the neural network generating, as an output therefrom, the control signal to cause the fluctuations of heart rate of the substitute heart, based on the physical information obtained by the information obtaining device, as an input signal thereto, according to the function having the learned constants.

9. A substitute-heart system comprising:

a total-substitution artificial heart which is adapted to be provided in a living body to totally substitute the natural heart of the living body; and a control apparatus which controls the total-substitution artificial heart, the control apparatus comprising:

an information obtaining device which non-invasively obtains, from the living body, physical information relating to blood circulation in the living body, and a control device which supplies, to the total-substitution artificial heart, a control signal to control a cardiac output that is a volume of blood outputted from the artificial heart per unit time, based on the physical information obtained by the information obtaining device, according to a predetermined relationship between cardiac output and physical information.

10. A substitute-heart system according to claim 9, wherein the predetermined relationship between cardiac output and physical information comprises a relationship which is predetermined based on a cardiac output of the natural heart of the living body, and the physical information obtained before the natural heart of the living body is totally substituted by the total-substitution artificial heart.

11. A substitute-heart system according to claim 9, wherein the predetermined relationship between cardiac output and physical information comprises a relationship between fluctuations of heart rate and physical information which is obtained by learning fluctuations of heart rate of the natural heart of the living body, and the physical information obtained before the natural heart of the living body is totally substituted by the total substitution artificial heart, and wherein the control device comprises a heart-rate control device which supplies, to the total-substitution artificial heart, the control signal to cause fluctuations of heart rate of the artificial heart, based on the physical information obtained by the information obtaining device, according to the relationship between fluctuations of heart rate and physical information.

* * * * *